| United States Patent [19] | [11] Patent Number: 4,910,310 |
| Campbell et al. | [45] Date of Patent: Mar. 20, 1990 |

[54] SYNTHESIS OF N-SUBSTITUTED 1,5-DIDEOXY-1,5-IMINO-L-FUCITOL DERIVATIVES

[75] Inventors: Arthur L. Campbell, Glenview; James R. Behling, Lindenhurst; Kevin A. Babiak, Evanston; John S. Ng, Chicago; Richard A. Mueller, Glencoe, all of Ill.; George W. J. Fleet, Oxford, United Kingdom

[73] Assignee: G. D. Searle & Co., Skokie, Ill.

[21] Appl. No.: 252,846

[22] Filed: Oct. 3, 1988

[51] Int. Cl.[4] .................. C07D 491/056; C07D 211/42
[52] U.S. Cl. ...................................... 546/116; 546/242
[58] Field of Search ................................. 546/116, 242

[56] References Cited

PUBLICATIONS

Paulsen et al., Annalen, pp. 1121–1126, Dec. 1988.

*Primary Examiner*—Mary C. Lee
*Assistant Examiner*—Bernard I. Dentz
*Attorney, Agent, or Firm*—Scott J. Meyer; James W. Williams, Jr.

[57] ABSTRACT

Novel intermediates and method for the chemical synthesis of N-substituted 1,5-dideoxy-1,5-imino-L-fucitol derivatives are provided. A preferred intermediate is 1,5-dideoxy-1,5-imino-3, 4-O-isopropylidene-L-fucitol which is used to prepare the HIV inhibitor 1,5-dideoxy-1,5-imino-[N-ω-methyl caproate]-L-fucitol. These compounds are prepared in a short synthesis from the known compound 2,3-O-isopropylidene-D-lyxono-1,4-lactone or in a multi-step synthesis from D-galactose.

13 Claims, No Drawings

SYNTHESIS OF N-SUBSTITUTED 1,5-DIDEOXY-1,5-IMINO-L-FUCITOL DERIVATIVES

BACKGROUND OF THE INVENTION

This invention relates to novel intermediates and method for the chemical synthesis of N-substituted 1,5-dideoxy-1,5-imino-L-fucitol derivatives.

The polyhydroxylated piperidine, 1,5-dideoxy-1,5-imino-L-fucitol, is a potent competitive inhibitor of α-L-fucosidase, although it has no inhibitory action on a range of other glycosidases. The synthesis of 1,5-dideoxy-1,5-imino-L-fucitol from commercially available methyl α-D-glucopyranoside is described by Fleet et al., *J. Chem. Soc., Chemical Communications* 13, 841-842 (1985). It is also useful in the production of inhibitors of the human immuno-deficiency virus (HIV) as described in co-pending application Ser. No. 136,219, filed Dec.21, 1987 now abandoned. One such HIV inhibitor is the following N-substituted derivative of 1,5-dideoxy-1,5-imino-L-fucitol:

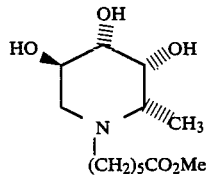

1,5-Dideoxy-1,5-imino-[N-ω-methyl caproate]-L-fucitol

This derivative was prepared by reaction of 1,5-dideoxy-1,5-imino-L-fucitol in methanol solvent medium with 6-oxyhexanoate.

DESCRIPTION OF THE INVENTION

In accordance with the present invention novel intermediates and method for the chemical synthesis of N-substituted 1,5-dideoxy-1,5-imino-L-fucitol derivatives are provided. A preferred such intermediate is 1,5-dideoxy-1,5-imino-3,4-0-isopropylidene-L-fucitol which can be used to prepare the HIV inhibitor 1,5-dideoxy-1,5-imino-[N-ωmethyl caproate]-L-fucitol.

The method comprises a short synthesis from the known compound 2,3-0-isopropylidene-D-lyxono-1,4-lactone or a multi-step synthesis from the inexpensive, commercially available sugar D-galactose.

The short synthesis from the known compound 2,3-0-isopropylidene-D-lyxono-1,4-lactone comprises esterifying said lactone at the unprotected C-5 hydroxyl group followed by introducing the azide group at C-5, reducing the lactone to the methyl ketal and then reducing the azide group by catalytic hydrogenation to provide the novel cyclic secondary amine 1,5-dideoxy-1,5-imino-3,4-O-isopropylidene-L-fucitol. The latter compound can then be reacted with methyl 6-oxohexanoate accompanied by catalytic hydrogenation to provide the novel intermediate compound 1,5-dideoxy-1,5-imino-3,4-O-isopropylidene-[N-ω-methyl caproate]-L-fucitol. Removal of the isopropylidene protecting group gives the active HIV inhibitor compound 1,5-dideoxy-1,5-imino-[N-ω-methyl caproate]-L-fucitol.

The multi-step synthesis from D-galactose comprises oxidizing the D-galactose in KOH solution to open the pyranose ring and form potassium D-lyxonate, subjecting the latter compound to alcoholic solution under acid conditions to provide furanose ring closure and form the D-lyxono-1,4-lactone, and then introducing a protecting group at C-2 and C-3 by reaction with ketone in the presence of a dehydrating agent. Use of acetone as the ketone in the latter step gives the compound 2,3-0-isopropylidene-D-lyxono-1,4-lactone. From that point on the multi-step system includes the general reaction steps of the above short synthesis.

The short synthesis from the known compound 2,3-O-isopropylidene-D-lyxono-1,4-lactone preferably comprises:

(a) esterifying said lactone at C-5 with triflic anhydride to give the triflate ester and then introducing the azide group at C-5, (b) reducing the lactone with methyl lithium in tetrahydrofuran solvent medium, and (c) reducing the azide group by catalytic hydrogenation to provide the six membered novel cyclic secondary amine 1,5-dideoxy-1,5-imino-3,4O-isopropylidene-L-fucitol.

The multi-step synthesis from D-galactose preferably comprises:

(a) oxidizing D-galactose in alcoholic KOH to open the pyranose ring and form potassium D-lyxonate, (b) reacting the potassium D-lyxonate in alcoholic solution with gaseous HCl to provide furanose ring closure and form the D-lyxono-1,4lactone, (c) introducing a protecting group at C-2 and C-3 by reaction of the lactone with ketone and $CuSO_4$, (d) esterifying the lactone at C-5 with triflic anhydride to give the triflate ester and then introducing the azide group at C-5, (e) reducing the lactone with methyl lithium in tetrahydrofuran solvent medium, (f) reducing the azide group by catalytic hydrogenation to provide a six membered cyclic secondary amine, (g) forming the N-substituted derivative by reacting the secondary amine with methyl 6-oxohexanoate accompanied by catalytic hydrogenation, and (h) removing the protecting group by acid hydrolysis.

Compounds prepared in steps (a), (b) and (c) of the multi-step synthesis, above, are known. Thus, potassium D-lyxonate is described by Humplett, *Carbohyd. Res.* 4, 157 (1967), and the D-lyxono-1,4lactone is disclosed by Thompson and Wolfram, *J. Amer. Chem. Soc.* 68, 1509 (1946), and Isbell, *J. Res. Natl. Bur. Stds.* 29, 227 (1942). The 2,3-0-isopropylidene protected D-lyxono-1,4lactone is disclosed by Morgenlie, *Acta Chem. Scand. B* 29, 367 (1975), and Schaffer, *J. Res. Natl. Bur. Stds. Sect. A.* 65, 507 (1961).

The following schematic outline illustrates the foregoing multi-step synthesis of 1,5-dideoxy-1,5-imino-[N-ω-methyl caproate]-L-fucitol starting with D-galactose.

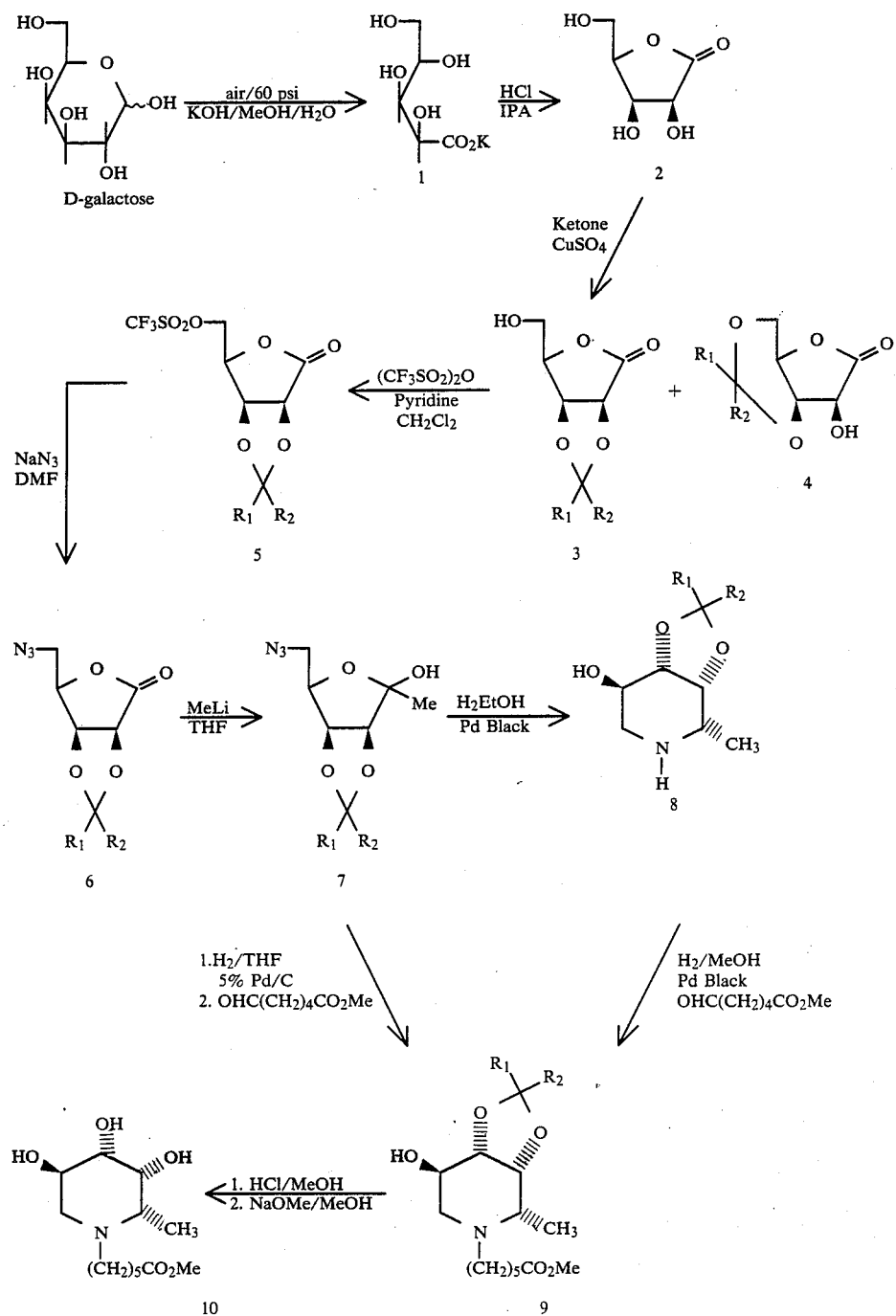

In the above schematic outline, $R_1$ and $R_2$ are individually alkyl groups having from one to about six carbon atoms or taken together with the connecting carbon are cycloalkyl having from 5 to about 8 carbon atoms.

Compounds 8 and 9, which are intermediates for the preparation of the N-substituted 1,5-dideoxy-1,5-imino-L-fucitol derivatives, are novel compounds. These intermediates are stable, crystalline solids which can be readily isolated and purified on a large scale.

A preferred compound of the structure 8 is 1,5-dideoxy-1,5-imino-3,4-O-isopropylidene-L-fucitol. A preferred compound of the structure 9 is 1,5-dideoxy-1,5-imino-3,4-0-isopropylidene-(N-ω-methyl caproate)-L-fucitol.

Although specific reactants to prepare the N-substituted 1,5-dideoxy-1,5-imino-L-fucitol derivatives and the intermediate compounds are described herein, other such suitable reactants for use in the foregoing syntheses will be apparent to the person skilled in the art after reading the present disclosure. These reactants are used in proportions such as to satisfy the stoichiometry of the above reaction steps.

In the oxidation of D-galactose in KOH solution to form potassium D-lyxonate 1, oxygen can be employed, but the use of air under moderate pressure of about 30 to 120 psi is preferred. Although KOH in aqueous solution can be used, alcoholic KOH is preferred. Reaction at a temperature of about 20° to 70° C. is suitable, and about 35° C. is preferred.

Formation of the lactone 2 in acidified alcoholic solution also can employ alcohols other than isopropyl alcohol (IPA) such as ethanol, propanol, tert-butanol and the like. Methanol is undesired due to its tendency to produce mixtures of the desired product, methyl ester of compound 1, the ortho-ester(s) and their solvolysis products. The presence of water is not disabling. Other acids which can be used in this step are mineral acids such as hydrogen bromide, sulfuric acid and phosphoric acid; organic acids such as toluene sulfonic acid, camphor sulfonic acid, trifluoracetic acid, chloro-substituted-acetic acids, nitro-substituted acids and the like. Reagents that produce acid condition when mixed with a protic solvent such as isopropyl alcohol also can be used, for example, acetyl chloride, phosphoryl chlorine, thionyl bromide and thionyl chloride. Reaction at a temperature of about -20° to 15° C. is suitable, and about 0° C. is preferred.

Introduction of the protecting group at C-2 and C-3 can employ ketones and dialkyketals of ketones such that $R_1$ and $R_2$ will be satisfied as provided hereinbefore. A symmetrical ketone such as acetone is preferred. Use of an asymmetric ketone may give rise to isomers. Other suitable ketones to provide a protecting group such that $R_1$ and $R_2$ are $C_{1-6}$ alkyl are, for example, 3-pentanone, 4-heptanone, 5-nonanone, 6-undecanone and 7-tridecanone (dihexyl ketone). Similarly, cyclic ketones such as, for example, cyclopentanone, cycloheptanone, cyclooctanone and, preferably, cyclohexanone, can be used to satisfy the $C_{5-8}$ cycloalkyl protecting group when $R_1$ and $R_2$ are taken together with the connecting carbon at C-2 and C-3. Dehydrating agents other than anhydrous $CuSO_4$ can be used, for example, molecular sieves, cation exchange resins and the like. Reaction at a temperature of about 45° to 60° C. is generally suitable. For higher boiling ketones, a cosolvent such as tetrahydrofuran (THF) can be used as an aid in reaction temperature maintenance. By-product compound 4 can be recycled to compound 3 by re-subjecting it to the foregoing reaction steps.

In the esterification step to produce compound 5, trifluoromethylsulfonyl anhydride (triflic anhydride) is the preferred electrophile, but tosyl chloride, benzene sulfonyl chloride, mesyl chloride and the like can be used. Reaction in pyridine base and methylene chloride solvent is preferred, but other bases such as lutidines, tetramethylpiperidine, triethylamine and the like, and other solvents such as chloroform, tetrahydrofuran, ether, toluene and similar solvents or solvent mixtures can be used. Reaction at a temperature of about −120° to −20° C. is suitable, and about −78° to −50° C. is preferred.

Introduction of the azide group at C-5 to produce compound 6 is readily and inexpensively carried out by the procedure illustrated. Alternative azide cations are potassium, tetra-butylammonium, lithium and the like. Trimethylsilyl azide also can be used. The dipolar aprotic solvents tetramethyl urea, N-methylpyrrolidine, dimethylactamids, acetonitrile, phosphors and phosphoric triamides (with proper safeguards), DMSO and tetramethylene sulfone and sulfoxide are alternatives to the illustrated DMF. Displacement temperatures of about −40° to 28° C. are suitable, and about −15° to 10° C. is preferred.

In the reduction of the lactone to the methyl ketal 7, Grignard reagents, for example, methyl magnesium bromide, methyl magnesium iodide and the like can be used although the methyl lithium is preferred. The preferred solvent is THF, but others such as dimethoxyethane (DME), the glymes and diethyl ether also are suitable. Toluene and the like aromatic solvents as well as alkanes in which the reactants are soluble also can be used as can solvent mixtures such as ether/cyclohexane, THF/hexane and ether/toluene. Reaction at a temperature of about −120° to −15° C. is suitable, and about −78° to −50° C. is preferred.

The synthesis of compound 8 from compound 7 is a reductive process, preferably carried out with palladium black in ethanol solvent using a flow of hydrogen followed by a period of hydrogen under low pressure. The preparation of compound 9 using compound 8 as the intermediate is preferably carried out with Pd in methanol at about 5 psi hydrogen pressure. The direct conversion of 7 to 9 is achieved in THF. Alternative solvents for these are lower alcohols, THF, toluene and ethyl acetate. Solvent selection is influenced by the need to control ester exchange in the product, e.g., compound 10. If a methyl ester is desired, either a non-alcoholic or methanolic solvent is used. If ester exchange is desired or is of no consequence due to a later hydrolysis step, for example, any lower alcohol or lower alcohol mixture can be used. Other suitable catalysts are 5% Pd/Carbon, Pt20, Ni(Raney), Pt/Carbon, Pt/alumina, Pd/alumina and Rh/carbon. The preferred temperature of reaction is about room temperature, but 0° to 40° is suitable.

The following detailed examples will further illustrate the invention although it will be understood that the invention is not limited to these specific examples.

EXAMPLE 1

The preparation of potassium D-lyxonate 1 from galactose.

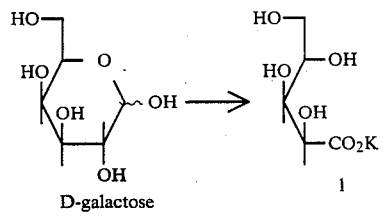

D-galactose

D-galactose

Air was sparged at 100 mL/min through a rapidly stirred solution of potassium hydroxide (41.9 g, 65.5 mmol) and D-galactose (45.0 g, 25.0 mmol) in a mixture of methanol/water (375 mL/180 mL) at 60 psi in a Parr bomb (1 L). The temperature was maintained at 35°–36° C. throughout the reaction. After sparging for 24 hours (h), methanol (50 mL) was added and sparging continued for a total of 45 h. The reaction mixture was cooled and vented. The bomb was opened and the light yellow mixture was filtered to remove a small amount of solids. The bomb and filter were rinsed with water (5 mL) in which most of the solids dissolved. The filtrate was stirred and diluted with methanol (850 mL). Crystallization occurred after approximately 500 mL of methanol had been added. After stirring for 4 h, the crystals were collected by filtration and vacuum dried to provide 29.3 g (57% yield) of potassium D-lyxonate 1 as a white solid: DISC mp 171.25° C.; Analysis calculated for C₅H₉O₆K: C, 29.41; H, 4.44. Found: C, 28.86; H, 4.16. This white solid material was used in Example 2 without further purification.

EXAMPLE 2

The preparation of D-lyxono-1,4-lactone 2.

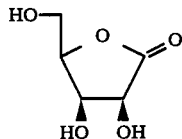

2

To a three necked flask (2 L, equipped with an ice/water bath, mechanical stirrer and vented to a trap containing an aqueous solution of potassium hydroxide, was added potassium (D)-lyxonate (177.18 g, 0.87 mol) and isopropanol (1.2 L). To this cooled vigorously stirred slurry was introduced gaseous HCl, via a sparge tube, at such a rate that the temperature did not exceed 40° C. HCl sparging was continued for 40 min at which time HCl fumes were detected at the caustic trap and the internal temperature began to fall. Sparging was discontinued and the mixture slowly heated to reflux (Caution: HCl fumes were vigorously expelled when the mixture approached the reflux temperature). After refluxing for 10 min, the mixture was cooled and concentrated under reduced pressure to a volume of about 250 mL. The residue was heated to attain solution and allowed to slowly cool to room temperature, during which time crystallization occurred. This highly crystalline product was filtered, washed with cold isopropanol (75 mL), air dried for 1 h and then vacuum dried overnight to provide 90.9 g of desired 2. The mother liquor and washings were reduced in volume to 75 mL, crystallized, filtered and dried as described above to give an additional 9.74 g of 2. The first and second crops were combined to provide 100.64 g of D-lyxono-1,4lactone 2 (77.6): DISC mp 112.51° C. [lit. (1), (2) mp 110–112 and 114° C.]; Analysis calculated for C₅H₈O₅: C, 40.54; H, 5.44. Found: C, 40.38; H, 5.51%

1. Thompson and Wolfrom, *J. Amer. Chem. Soc.* 68, 1509 (1946).
2. Isbell, *J. Research Natl. Bur. Standards*, 29, 227 (1942).

EXAMPLE 3

The Preparation of 2,3-O-isopropylidene-D-lyxono-1,4-lactone 3.

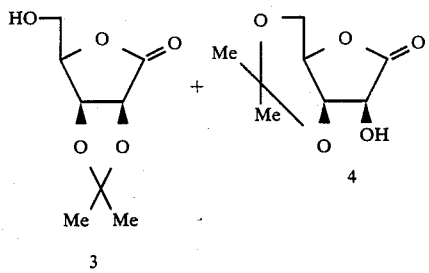

To a three necked Morton flask (5 L) equipped with a mechanical stirrer and reflux condenser was added D-lyxono-1,4-lactone 2 (85 g, 0.57 mol), acetone 3.4 L) and anhydrous CuSO₄ (170 q, 1.07 mol). This vigorously stirred heterogenous mixture was refluxed for 48 h, cooled to room temperature, filtered through a pad of Celite® diatomaceous earth and concentrated to provide 117 g of a crude off-white solid. The crude mixture was purified by preparative chromatography (silica gel, acetone/hexane: 20/80 to 50/50) to provide four fractions (a-d): (a) 2,3-0-isopropylidene-D-lyxono-1,4-lactone 3, 41.3 g (38%): mp 96°–97° [lit. (3), (4) mp 88°93° and 99°–100° C.]; Analysis calculated for C₈H₁₂O₅: C, 51.06; H, 6.03. Found: C, 50.86; H, 6.41. (b) mixture 3/4:95/5, 10.84 g (10%); (c) mixture 3/4:40/60, 25.6 g (23%); (d) pure 3,5-isopropylidene-D-lyxono-1,4-lactone 4, 10.7 g (10%): mp 140°–141° C. (recrystallized form ethyl acetate/hexane)[lit.(3) 137 °–138° C.]. Also, 11.4 g (13%) of 2 was recovered by flushing the column with methanol. Alternatively, 3 can be isolated in greater than 95% purity by crystallization of the crude reaction mixture using isopropanol. Also, 4 can be converted to a mixture of 3 and 4 (ratio 75/25) by re-subjecting it to the above reaction conditions.

3. Morgenlie, *Acta Chem. Scand.* B 29, 367 (1975).
4. Schaffer, *J. Res. Nat. Bur. Stand. Sect.* A 65, 507 (1961).

EXAMPLE 4

The preparation of 5-azido-5-deoxy-2,3-O-isopropylidene-D-lyxono-1,4-lactone 6.

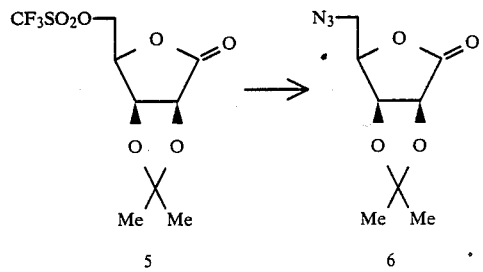

To a cooled (-25° C.) solution of 2,3-O-isopropylidene-D-lyxono-1,4-lactone 3 (10.0 g, 53.2 mmol) and pyridine (8.38 g, 8.56 mL, 106.4 mmol) in CH₂Cl₂ (125 mL) was added dropwise via syringe triflic anhydride (16.5 g, 9.82 mL, 58.5 mmol) at a rate such that the reaction temperature did not exceed −18° C. After the addition was complete the reaction was gradually warmed to 0° C. over 1.5 h. TLC (silica, ethyl acetate/hexane:1/1) indicated no 3 remaining and the presence of a single new product (R$_f$=0.45). The reaction mixture was poured into ice/water (250 mL), partitioned and the aqueous layer extracted with CH₂Cl₂ (2 × 50 mL). The organic layers were combined, washed with cold saturated aqueous CuSO₄ (3×50 mL), water (50 mL), brine (50 mL), dried (MgSO₄), filtered and concentrated to provide a bright red-orange glassy solid (R$_f$; silica=0.12, tetrahydrofuran (THF)/hexane: 30/70) which still contained solvent. Crude triflate 5 was dissolved in N,N-dimethyformamide (DMF) (100 mL), cooled with an ice/water bath and sodium azide (6.92 g, 106.4 mmol) was slowly added. After the addition was complete, the cooling bath was removed and the mixture stirred at room temperature for 2.5 h. The DMF was removed by bulb-to-bulb distillation under vacuum (31° C. @0.7 mm Hg). The receiver bulb was cooled with a dry ice/acetone bath to increase the efficiency of the distillation. The resultant thick pasty residue was dissolved in CH₂Cl₂ (150 mL) and filtered to remove the inorganic salts. The filter cake was washed with CH$_2$Cl$_2$ (150 mL) and the combined filtrates were concentrated under vacuum. If desired, the resulting partially purified product can be used directly in the synthesis of compound 7. In this example, the residue was further purified by subjecting it to the above bulb-to-bulb distillation technique (for removal of the last traces of DMF) to provide 15.5 g of a crude red solid which was purified by flash chromatography [silica gel (100 g), ethyl acetate/hexane:1/1]to provide 10.09 g of 6 (89% yield) of a pale yellow solid: (R$_f$,silica=0.21, THF/hexane: 30/70), DISC mp 59.7° C.; Analysis Calculated for C$_8$H$_{11}$N$_3$O$_4$: C, 45.07; H, 5.20; N, 19.71. Found: C, 44.98; H, 5.28; N, 19.28.

EXAMPLE 5

Preparation of 6-azido-1,6-dideoxy-3, 4-O-isopropylidene-D-lyxo-hexoketo-2,5-furanose 7.

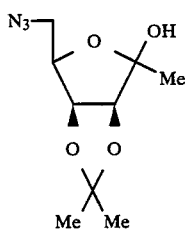

7

Methyl lithium (200 mL, 1.5 M in ether, 0.3 mole) was added to a cold ( −78° C.) solution of 5-azido-5-deoxy-2,3-O-isopropylidene-D-lyxono-1,4lactone δ (58.1 g, 0.27 mole) in THF (1.2 L, freshly distilled from sodium/benzophenone) under at inert atmosphere of nitrogen. The reaction mixture was stirred at −78° C. for 30 min and then quenched by pouring into a solution of ammonium chloride (71 g, 1.33 mole) in water 1.2 L). The layers were separated and the aqueous fraction was extracted with CH$_2$Cl$_2$ (2×250 mL). The combined organic extracts were washed with water 1 L), dried (MgSO$_4$), filtered and concentrated to provide 60 g (97% yield) of 7 as a white crystalline solid: DISC mp 86.2° C.; Analysis calculated for C$_9$H$_{14}$O$_5$N$_3$: C, 47.16; H, 6.41; N, 18.3. Found: C, 47.37; H, 6.53; N, 17.41.

EXAMPLE 6

The preparation of 1,5-dideoxy-1,5-imino-3,4-O-isopropylidene-L-fucitol 8.

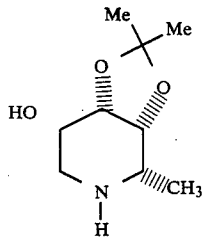

8

A. solution of 6-azido-1,6-dideoxy-3,4-O-isopropylidene-D-lyxo-hexoketo-2,5-furanose 7 (30.9 g, 0.14 mole) in absolute ethanol (1.7 L) was added to a Parr bomb (2 L) containing9 palladium black and ethanol (50 mL). The catalyst was pre-wetted with ethanol (50 mL) under an atmosphere of argon and transferred to the bomb as a slurry. The bomb was sealed, flushed with nitrogen and then sparged with hydrogen at 100 mL/min for 1.0 h to reduce the azide. This reaction is mildly exothermic; therefore, an internal cooing coil was required to maintain the temperature between 25°–30° C. After 1 h the sparging was discontinued and the reaction maintained under a positive pressure of hydrogen (5 psi) for 24 h. The Parr bottle was vented, purged with nitrogen (3x), opened and the catalyst removed by filtration. The filtrate was concentrated under vacuum o provide 23.8 g (91% yield) of 8 as a light yellow solid. This material was normally carried on crude but can be purified by chromatography [silica gel (600 g) MeOH/CHC$_3$: 8/92 to 40/60]To provide 20.5 g of a white solid: DISC mp 184° C.; Analysis calculated for C$_9$H$_{17}$NO$_3$: C, 57.73; H, 9.15; N, 7.48. Found: C, 57.03; H, 9.18; N, 7.45.

EXAMPLE 7

The preparation of 1,5-dideoxy-1,5-imino-3,4-0-isopropylidene-(N-ω-methylcaproate)-L-fucitol 9.

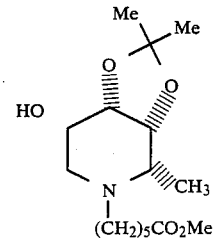

9

To a Parr bottle (2.2 L), under a nitrogen atmosphere, was added a slurry of palladium black (10.5 g) in methanol (250 mL, aldehyde free) followed by a solution of 1,5-dideoxy-1,5-imino-3, 4-0-isopropylidene-L-fucitol 8 (15.4 g, 82.1 mmol) in methanol (750 mL) and neat methyl 6-oxohexanoate (14.2 g, 98.6 mmol). The Parr bottle was placed on the shaker, sealed, flushed with nitrogen (3x) and filled with hydrogen (5 psi). The mixture was agitated at room temperature for 24 h, during which time the theoretical amount of hydrogen had been taken up. The Parr bottle was vented, purged with nitrogen (3x), opened and the catalyst removed by filtration. The filtrate was concentrated under vacuum to provide 24g of a yellow oil which was purified by chromatography (silica gel, 432 g, acetone/hexane: 30/70 to 50/50). 17.0 g (66%) of 9 was obtained as a colorless viscous oil: Analysis calculated for C$_{16}$H$_{29}$NO$_5$: C, 60.92; H, 9.28; N, 4.43. Found: C, 60.56; H, 9.45; N, 4.42.

EXAMPLE 8

Alternate preparation of 1,5-dideoxy-1, 5-imino-3,4-O-0-isopropylidene-(N-ω-methyl caproate)-L-fucitol -9.

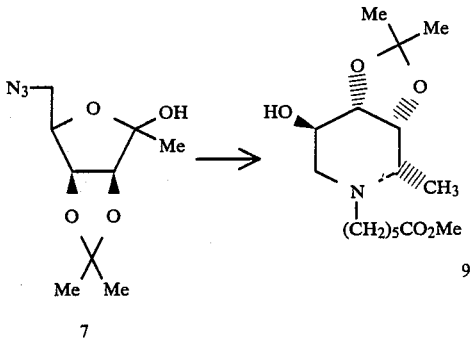

This alternate procedure involves the direct preparation of 9 from 7 without isolating the first reductive amination product 8 using 5% palladium on carbon as the hydrogenation catalyst and tetrahydrofuran as the solvent. To a Parr bomb (1 L) containing 5% palladium on carbon (2.1 g) and 6-azido-1,6-dideoxy-3,4-O-isopropylidene-D-lyxo-hexoketo-2,5-furanose 7 (10.0 g, 0.04 mole) under an argon atmosphere was added dry tetrahydrofuran (500 mL). The Parr bomb was sealed, flushed which nitrogen and then sparged with hydrogen at 100 mL/min for 1.0 h to reduce the azide. This reaction is mildly exothermic. Therefore, an internal cooling coil was required to keep the temperature between 25°–30° C. After 1 h, the sparging was discontinued and the reaction maintained under a positive pressure of hydrogen (60 psi) for 18 h. The Parr bomb was vented, placed under vacuum and methyl 6-oxo-hexanoate (7.59 g, 0.05 mole) in tetrahydrofuran (40 mL) was drawn in. The bomb was purged with nitrogen (3x), hydrogen (3x) and then pressurized to 60 psi. The mixture was stirred at 25°–30° C. and 60 psi for 2h. Stirrinq was stopped and the Parr bomb was vented, purged with nitrogen (3x), opened, and the catalyst removed by filtration. The filtrate was concentrated under vacuum to provide 13.3 g of 9 as a light yellow oil which was purified by chromatography (silica gel (250 g), acetone/hexane: 30/70 to 50/50). 10.7 g (85% yield) of 9 was obtained as a colorless viscous oil which was identical to the material obtained in Example 7.

EXAMPLE 9

The preparation of 1,5-dideoxy-1,5-imino-(N-ω-methyl caproate) L-fucitol 10.

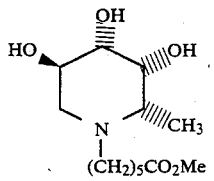

To a three necked round bottom flask equipped with magnetic stirrer, a Dean-Stark trap, and a reflux condenser was added a solution of 1,5-dideoxy-1,5-imino-3,4-0-isopropylidene-(N-ω-methyl caproate)-L-fucitol 9 (44.6 g, 0.14 mole) in anhydrous methanol (250 mL, freshly distilled from Mg under a nitrogen atmosphere) followed by a cooled (0° C.) methanolic HCl solution [400 mL, freshly prepared by adding acetyl chloride (12.2 g, 0.15 mole) to anhydrous methanol at 0° C. This mixture was refluxed for 3 h and then methanol was slowly removed for 2 h by opening the bottom of the Dean-Stark trap. Additional anhydrous methanol was added as needed to maintain about 500 mL in the flask. TLC analysis (silica, chloroform/methanol/ammonium hydroxide: 27/77/3) indicated the solvolysis was complete. The solvent was removed under reduced pressure to provide 42 g of 10 as the hydrochloride salt which was neutralized as follows: To a cooled (0° C.) solution of the crude amine hydrochloride in anhydrous methanol (200 mL), under an argon atmosphere, was added dropwise via syringe NaOCH$_3$ (143.0 mL, 0.143 mole, 1M solution freshly prepared in methanol) at a rate such that the reaction temperature did not exceed 2° C. during the addition. The mixture was stirred at 0° to 2° C. for 30 min followed by concentration, in vacuo. The oily residue was triturated with a solution of ether/methylene chloride:1/1 (300 mL) and then filtered through a sintered glass funnel to remove the inorganic sats. The flask and filter cake were rinsed with ether/methylene chloride:1/1 (200 mL) and the combined filtrates were concentrated at reduced pressure to give an amber oil which was purified by chromatography (silica gel (600 g), CH$_3$OH/CHCl$_3$: 10/90 to 40/60) to provide 29.03 g (75% yield) of the title compound 10 as a viscous pale yellow oil which solidified on standing: DISC mp=59.5° C.; Analysis calculated for C$_{13}$H$_{25}$NO$_5$: C, 56.71; H, 9.15; N, 5.09. Found: C, 56.58; H, 9.41; N, 5.07

EXAMPLE 10

When the foregoing synthesis is carried out in a manner substantially similar to that employed in Examples 1 to 9, above, but with protecting groups other than isopropylidene by substituting other ketones for an equivalent amount of the acetone used in Example 3 , the following illustrative intermediate compounds analogous to compounds 8 and 9 are prepared:

| Ketone | Compound |
| --- | --- |
| 3-Pentanone (Diethyl ketone) | 1,5-Dideoxy-1,5-imino-3,4-0-3-pentylidene-L-fucitol, and 1,5-Dideoxy-1,5-imino-3,4-0-3-pentylidene-(N-ω-methyl caproate)-L-fucitol. |
| 7-Tridecanone (Dihexyl ketone) | 1,5-Dideoxy-1,5-imino-3,4-0-7-tridecylidene-L-fucitol, and 1,5-Dideoxy-1,5-imino-3,4-0-7-tridecylidene-(N-ω-methyl caproate)-L-fucitol. |
| Cyclohexanone | 1,5-Dideoxy-1,5-imino-3,4-0-cyclohexylidene-L-fucitol, and 1,5-Dideoxy-1,5-imino-3,4-0-cyclohexylidene-(N-ω-methyl caproate)-L-fucitol. |
| Cyclooctanone | 1,5-Dideoxy-1,5-imino-3,4-0-cyclooctylidene-L-fucitol, and 1,5-Dideoxy-1,5-imino-3,4-0-cyclooctylidene-(N-ω-methyl caproate)-L-fucitol. |

Various other examples will be apparent to the person skilled in the art after reading the present disclosure without departing from the spirit and scope of the invention. It is intended that all such other examples be included within the scope of the appended claims.

What is claimed is:

1. A method for the chemical synthesis of 1,5-dideoxy-1,5-imino-3,4-0-isopropylidene-L-fucitol from 2,3-0-isopropylidene-D-lyxono-1,4-lactone comprising esterifying said lactone at the unprotected C-5 hydroxyl group followed by introducing the azide group at C-5, reducing the lactone to the methyl ketal and then reducing the azide group by catalytic hydrogenation to provide the cyclic secondary amine 1,5-dideoxy-1,5-imino-3,4-O-isopropylidene-L-fucitol.

2. The method of claim 1 comprising:
 (a) esterifying said lactone at C-5 with triflic anhydride to give the triflate ester and then introducing the azide group at C-5,
 (b) reducing the lactone with methyl lithium in tetrahydrofuran solvent medium, and
 (c) reducing the azide group by catalytic hydrogenation to provide the six membered cyclic secondary amine 1,5-dideoxy-1,5-imino-3,4-O-isopropylene-L-fucitol.

3. 1,5-dideoxy-1,5-imino-3,4-O-isopropylidene-L-fucitol.

4. A method for the chemical syntheses of 1,5-deoxy-1,5-imino-3,4-0-isopropylidene-(N-ω-methyl caproate)-L-fucitol comprising reacting the compound of claim 3 with methyl 6-oxohexanoate accompanied by catalytic hydrogenation.

5. 1,5-dideoxy-1,5-imino-3,4-O-isopropylidene-(N-ω-methyl caproate)-L-fucitol.

6. A method for the chemical synthesis of 1,5-dideoxy-1,5-imino-(N-ω-methyl caproate)-L-fucitol comprising removing the isopropylidene protecting group from the compound of claim 5 by acid hydrolysis.

7. A method for the chemical synthesis of 1,5-dideoxy-1,5-imino-3,4-O-isopropylidene-L-fucitol from D-galactose comprising oxidizing said D-galactose in KOH solution to open the pyranose ring and form potassium D-lyxonate, subjecting the latter compound to alcoholic solution under acid conditions to provide furanose ring closure and form the D-lyxono-1,4-lactone, introducing a protecting group at C-2 and C-3 by reacting with ketone in the presence of dehydrating agent., esterifying the unprotected C-5 hydroxyl group followed by introducing the azide group at C-5, reducing the lactone to the methyl ketal and then reducing the azide group by catalytic hydrogenation to provide the cyclic secondary amine 1,5-dideoxy-1,,5-imino-3,4-O-isopropylidene-L-fucitol.

8. The method of claim 7 including the additional step of reacting the 1,5-dideoxy-1,5-imino-3,4-O-isopropylidene-L-fucitol with methyl-6-oxohexanoate accompanied by catalytic hydrogenation to produce 1,5-dideoxy-1,5-imino-3,4-O-isopropylidene-(N-ω-methyl caproate)-L-fucitol.

9. The method of claim 8 including the additional step of removing the isopropylidene protecting group from 1,5-dideoxy-1,5-imino-3,4-O-isopropylidene-(N ω-methyl caproate)-L-fucitol by acid hydrolysis to produce 1,5-dideoxy-1,5-imino-(N-ω-methyl caproate)-L-fucitol.

10. The method of claim 9 comprising:
 (a) oxidizing D-galactose in alcoholic KOH to open the pyranose ring and form potassium D-lyxonate,
 (b) reacting the potassium D-lyxonate in alcoholic solution with gaseous HCl to provide furanose ring closure and form the D-lyxono-1,4lactone,
 (c) introducing a protecting group at C-2 and C-3 by reaction of the lactone with ketone and $CuSO_4$,
 (d) esterifying the lactone at C-5 with triflic anhydride to give the triflate ester and then introducing the azide group at C-5,
 (e) reducing the lactone with methyl lithium in tetrahydrofuran solvent medium,
 (f) reducing the azide group by catalytic hydrogenation to provide a six membered cyclic secondary amine,
 (g) forming the N-substituted derivative by reacting the secondary amine with methyl 6-oxohexanoate accompanied by catalytic hydrogenation, and
 (h) removing the protecting group by acid hydrolysis.

11. A method for the chemical synthesis of 1,5-dideoxy-1,5-imino-3,4-O-isopropylidine-(N-ω-methyl caproate)-L-fucitol comprising reacting 6-azido-1,6-dideoxy-3,4-O-isopropylidene-D-lyxo-hexoketo-2,5-furanose and methyl 6-oxohexanoate and carrying out catalytic hydrogenation in tetrahydrofuran solvent medium.

12. A compound of the structure

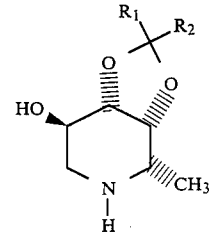

wherein $R_1$ and $R_2$ are individually alkyl groups having from one to about six carbon atoms of taken together with the connecting carbon are cycloalkyl having from five to about eight carbon atoms.

13. A compound of The structure

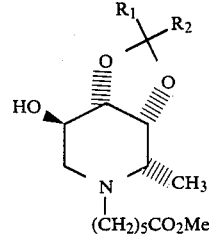

wherein $R_1$ and $R_2$ are individually alkyl groups having from one to about six carbon atoms or taken together with the connecting carbon are cycloalkyl having from five to about eight carbon atoms.

* * * * *